(12) United States Patent
Wexler

(10) Patent No.: US 6,773,449 B2
(45) Date of Patent: *Aug. 10, 2004

(54) APPARATUS FOR APPLYING CRANIAL OCCIPITAL PRESSURE

(76) Inventor: Robert Wexler, 4240 Navajo St., Toluca Lake, CA (US) 91602

( * ) Notice: Subject to any disclaimer, the term of this patent is extended or adjusted under 35 U.S.C. 154(b) by 0 days.

This patent is subject to a terminal disclaimer.

(21) Appl. No.: 09/865,477

(22) Filed: May 29, 2001

(65) Prior Publication Data

US 2002/0007195 A1 Jan. 17, 2002

Related U.S. Application Data

(63) Continuation-in-part of application No. 09/109,911, filed on Jul. 2, 1998, now Pat. No. 6,238,413.

(51) Int. Cl.⁷ .................................................. A61F 5/08
(52) U.S. Cl. ................................................. 606/204.15
(58) Field of Search ............................... 2/DIG. 11, 12, 2/171, 426, 422, 425, 6.3, 312; 602/74, 75, 17, 18; 128/97.1; 606/191–203, 204.15, 1; 607/108–110, 112; 601/134

(56) References Cited

U.S. PATENT DOCUMENTS

| | | | |
|---|---|---|---|
| 1,324,975 A | * 12/1919 | Morris | 2/174 |
| 3,159,160 A | 12/1964 | Ullom | |
| 4,606,077 A | * 8/1986 | Phillips | 2/12 |
| 4,646,728 A | * 3/1987 | Takeda | 128/97.1 |
| 4,716,898 A | 1/1988 | Chauve et al. | |
| 4,944,289 A | * 7/1990 | Matthews | 128/97.1 |
| 5,094,229 A | 3/1992 | Pomatto et al. | |
| 5,280,793 A | 1/1994 | Rosenfeld | |
| 5,405,311 A | * 4/1995 | Pecora et al. | 606/201 |
| 5,419,758 A | 5/1995 | Vijayan | |
| 5,695,520 A | * 12/1997 | Bruckner et al. | 601/134 |
| 5,737,777 A | 4/1998 | Hilleary | |
| 5,848,981 A | * 12/1998 | Herbranson | 606/201 |
| 6,238,413 B1 | * 5/2001 | Wexler | 601/134 |

* cited by examiner

Primary Examiner—Katherine Moran
(74) Attorney, Agent, or Firm—Morgan, Lewis & Bockius LLP

(57) ABSTRACT

An apparatus and method for applying occipital pressure to a human head. The human head has frontal, parietal, and occipital bones. The frontal bone generally is on a front portion of the head, the occipital bone generally is on a back portion of the head, and the parietal bones generally extend between the frontal and occipital bones. The apparatus comprises a harness adapted to overlie the frontal bone, and a pad adapted to apply a therapeutic force to the occipital bone. The pad has first and second ends attached to the harness. And the pad has first and second protrusions that extend generally toward the harness and that are adapted to overlie the occipital bone.

14 Claims, 3 Drawing Sheets

APPARATUS FOR APPLYING CRANIAL OCCIPITAL PRESSURE

CROSS-REFERENCE TO RELATED APPLICATIONS

This application is a continuation-in-part of U.S. patent application Ser. No. 09/109,911, filed Jul. 2, 1998, now U.S. Pat. No. 6,238,413, the disclosure of which is incorporated herein in its entirety.

FIELD OF THE INVENTION

This application relates to a headband or a fastening device for applying pressure to the back of a human head for therapeutic effects, and more particularly to a device that applies bilateral pressure to the occipital region to improve the circulation of cerebrospinal fluid.

BACKGROUND OF THE INVENTION

It is believed that the human body is continually subjected to physical and other forms of stress that can stimulate the occurrence of a variety of ailments or otherwise cause detrimental effects to one's physical health or well-being. It is believed that these physical stresses can include injuries stemming from birth trauma, automotive accidents, athletic exertions, or postural problems. It is further believed that other forms of stress can occur from psychological tension or emotional disturbances, which may be caused by depression or anxiety. The occurrence of stress is believed to manifest as muscle tension, which in turn may tighten the muscles around the head and neck. It is believed that severe or prolonged muscle tension in the area surrounding the cranium may distort the alignment of cranial bones.

Within the human cranium, it is believed that cerebrospinal fluid fills the ventricles of the brain and occupies the subarachnoid space. It is believed that cerebrospinal fluid is a clear watery fluid that remains in constant circulation throughout the brain and the spinal cord. It is further believed that cerebrospinal fluid acts as both a protective cushion against injury and a carrier of nutrients and proteins that provide nourishment to the brain for normal functioning.

It is believed that cerebrospinal fluid drains from the lateral ventricles through the interventricular foramina of Monro into the third ventricle. This fluid is then believed to combine with fluid produced by the choroid plexus of the third ventricle, and then pass through the cerebral aqueduct of Sylvius into the fourth ventricle. The fluid is then believed to escape through openings in the roof of the fourth ventricle, the median foramen of Magendie, and the two lateral foramina of Luschka. From the foramina of the fourth ventricle, it is believed that the fluid enters the subarachnoid space. Henry Gray and Charles Goss, *Gray's Anatomy*, Lea & Febiger, 1973.

It is believed that there are four major rhythmic pulsations from fluid circulation within the cranium. It is believed that blood flows from cardiovascular circulation between 60 to 72 times per minute to provide circulation throughout the brain and the entire body. It is also believed that oxygen is provided to the vascular system through respiratory circulation at 14 to 19 times per minute. And it is further believed that there are sutural pulsations at 14 to 19 times per minute and dural pulsations at 6 to 8 times per minute, which are measured as a cranial rhythm index. These rhythmic pulsations are believed to affect the circulation of cerebrospinal fluid.

With regard to rhythmic dural pulsation, it is believed that flexion/extension movement provides tension changes to the membrane within the dural system. Dural flexion is believed to occur when the distance from the internal margin of the lamboid and the superior posterior margin of the sphenobasilar articulation decrease in distance. This decrease in distance is believed to produce a slight tension to the external margin of the falx cerebrum, falx cerebellum, and the falx tentorium. The internal margin of the membrane is believed to produce a slight relaxation of the falx cerebrum, falx cerebellum, and the falx tentorium. It is believed that this membrane tension change allows the external cisterns and superior sagital sinus to decrease in volume and size. When this takes place, it is also believed that the ventricles of the brain increase in volume and size. It is believed that the cerebrospinal fluid moves with the fluctuations of this rhythmic cycle.

It is believed that if the skeletal structure in the cranium is improperly aligned, the cerebrospinal fluid cannot provide optimal circulation throughout the cerebrum. By applying pressure to the cranium, it is believe to be possible to stimulate greater circulation to reverse, or at least reduce the harmful effects of sub-optimal cerebrospinal fluid flow. It is believed that in 1939, Dr. William Garner Sutherland, DO, experimented with a technique of applying pressure to the occipital region of the head to cause a compression of the fourth ventricle, adjacent to the cerebellum. Traditionally called a "CV-4" technique, it is believed that a therapist can press against the occiput and thus apply resistance against movement to modify the activity of the craniosacral system. It is believed that this induces a "still-point" that can enhance the flow of cerebrospinal fluid throughout the cerebrum. Upon reaching a "still-point," it is believed that a patient can enjoy a sense of relaxation.

It is believed that a patient must remain immobile in order to induce a "still point." Thus, it is believed that previous methods or devices applying pressure to the occipital region require the assistance of a therapist, or devices that require a patient to remain immobile while receiving treatment. The inconvenience of relying upon another to provide treatment and remaining in a still position during a treatment process is believed to greatly reduce the benefits of the treatment and limit the opportunities for achieving a state of relaxation from the application of occipital pressure.

It is believed that there is a need for an apparatus and a method of applying occipital pressure that overcomes the problems and limitations of the previous methods and devices.

SUMMARY OF THE INVENTION

The present invention provides an apparatus for applying occipital pressure to a human head. The human head has a frontal, an occipital, and parietal bones. The frontal bone generally is on a front portion of the head, the occipital bone generally is on a back portion of the head, and the parietal bones generally extend between the frontal and parietal bones. The apparatus comprises a harness adapted to overlie the frontal bones, and a pad adapted to apply a therapeutic force to the occipital bone. The pad has first and second ends attached to the harness. And the pad has first and second protrusions that extend generally toward the harness and that are adapted to overlie the occipital bone.

The present invention also provides an apparatus for applying occipital pressure to a human head. The human head has a frontal, an occipital, and parietal bones. The frontal bone generally is on a front portion of the head, the occipital bone generally is on a back portion of the head, and the parietal bones generally extend between the frontal and occipital bones. The apparatus comprises a band adapted to surround the human head, at least one protrusion, and a cushion. The band has a first portion adapted to overly the occipital bone, a second portion adapted to overly the frontal bone, and connecting portions that extend between the first and second portions. The at least one protrusion extends inwardly from the first portion and is adapted to apply a therapeutic force to the occipital bone. The cushion extends inwardly from the second portion and is adapted to apply a reaction force to the frontal bone. The reaction force opposes the therapeutic force.

The present invention further provides a method of applying theraputic forces to a human head. The human head has a frontal, an occipital, and panetal bones. The frontal bone generally is on a front portion of the head, the occipital bone generally is on a back portion of the head, and the parietal bones generally extend between the frontal and occipital bones. The method comprises surrounding the human head with a band, the band having at least one inwardly directed protrusion and a cushion; orienting the cushion to overly the frontal bone; orienting the at least one inwardly directed protrusion so as to overly the occipital bone; and adjusting the band so as to enhance a flow of cerebrospinal fluid within the human head.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention.

DETAILED DESCRIPTION OF THE PREFERRED EMBODIMENT

Reference will now be made in detail to the preferred embodiments that are illustrated in the accompanying drawings, wherein like numerals indicate like elements throughout. Certain terminology is used in the following description to facilitate the description only and is not intended to be limiting in its use.

Figure 1:
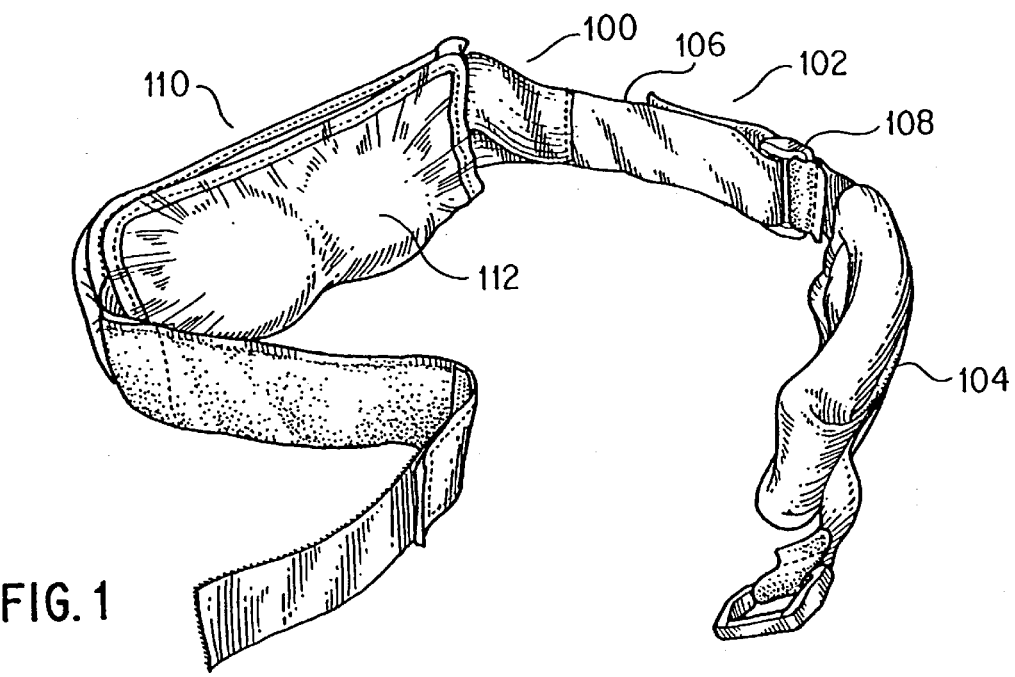
FIG. 1 is a perspective view of a preferred embodiment of an apparatus for applying cranial occipital pressure.

Referring to FIG. 1, a headband 100 preferably comprises a band 102 connected to a forehead pad 104. The illustrated headband 100 is example of many types and styles of devices that can be used to surround a head. The band 102 preferably includes a strap 106 and a buckle 108. The strap 106 interlinks within the buckle 108 to form the band 102 that connects the forehead pad 104 to a therapeutic pad 110. In the preferred embodiment shown in FIG. 1, there is a second band composed of a second strap and a second buckle for forming a symmetrical harness attached to the therapeutic pad 110. The strap 106 can be secured with respect to the buckle 108 by a hook and loop fastener, e.g., on an outer strap surface disposed away from the head. The strap 106 can also comprise materials such as leather or cotton, and may be secured by other means, such as by buttons or snaps.

The preferred therapeutic pad 110 is configured to apply bilateral pressure at the back of the head when worn. The therapeutic pad 110 can be made of any material suitable for maintaining a force against the head, including nylon, rayon, cotton, leather, etc. As shown in FIG. 1, the therapeutic pad 110 can be sewn closed around the sides and an upper portion, and can contain an inner material shaped to form two protrusions 112 appearing along the inner surface. The protrusions are symmetrical about the center of the pad to apply the desired bilateral pressure when worn.

Figure 2A:
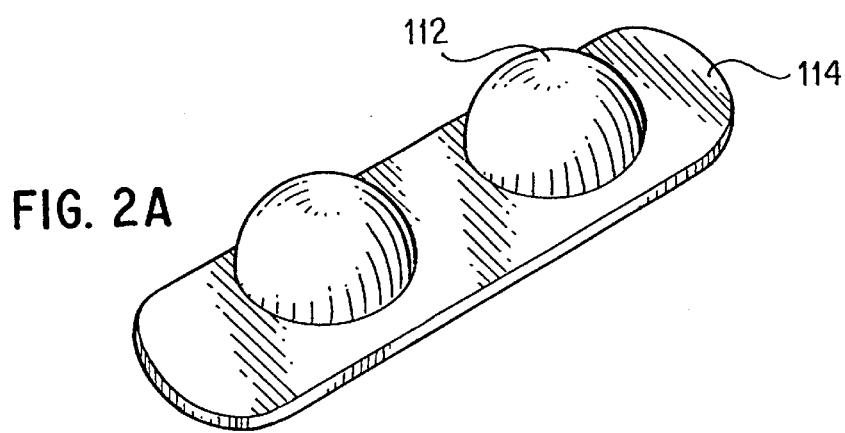
FIG. 2A is a perspective view of a plate with attached protrusions to apply occipital pressure.

Referring also to FIG. 2A, the two protrusions 112 can be two generally semispherical objects placed within the therapeutic pad 110. The semispheres can be made of rubber, foam, metal, plastic, or any other material sufficient to apply pressure against the occiput. The semispheres can also be filled with a fluid that be heated or chilled. In FIG. 2A, the two semispherical protrusions 112 are connected through an attachment plate 114, which can be made of metal, plastic, cloth, etc., that is placed within the pad 110. The spheres can also be sewn directly into the pad 110.

Figure 2B:
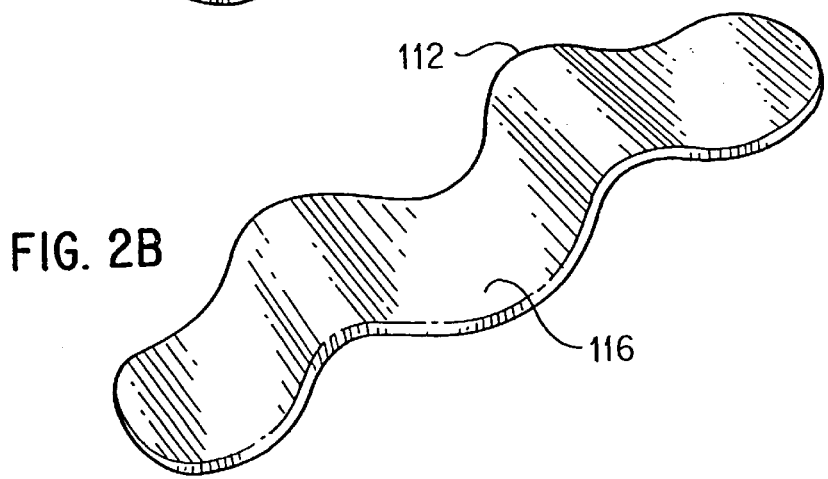
FIG. 2B is a perspective view of a curvilinear plate with integral protrusions to apply occipital pressure.

In an alternative embodiment shown in FIG. 2B, the protrusions 112 can be formed within the therapeutic pad 110 by a single curved structure, such as a piece of metal formed to provide the symmetrical protrusions. In FIG. 2B, a curved portion 116 serves to apply bilateral pressure to the occiput. The curved portion 116 can be sewn directly into the pad 110. The pressure points for applying occipital pressure can be adjusted by bending the curvilinear structure.

Figure 3:
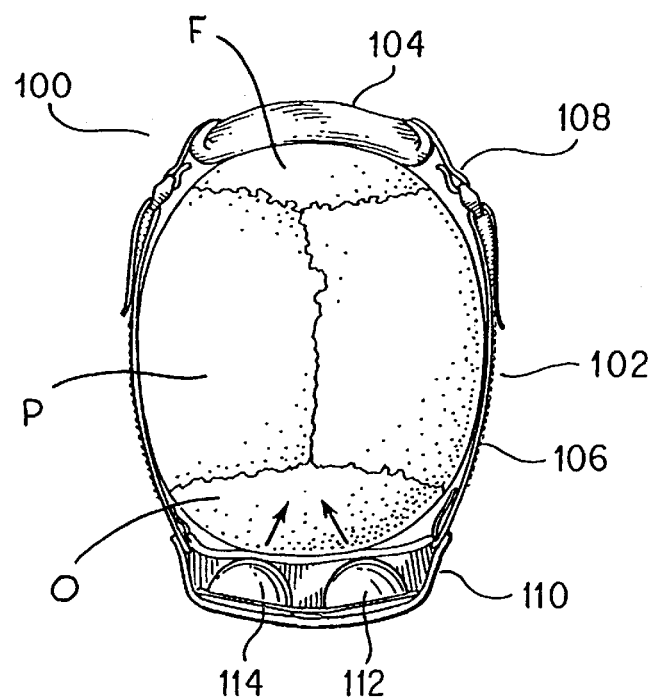
FIG. 3 is a top view illustrating a placement on a head of the apparatus shown in FIG. 1.
Figure 4:
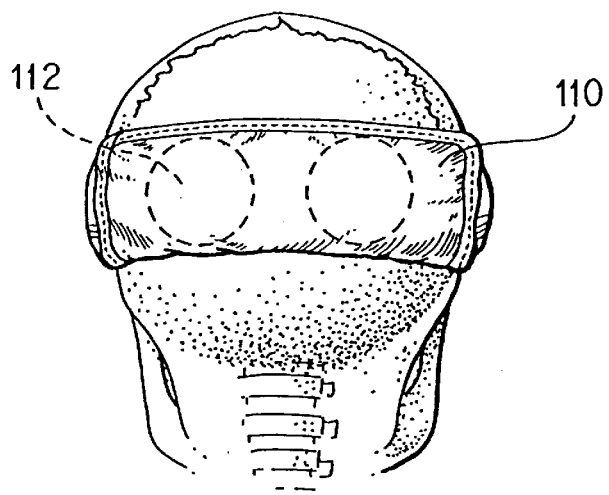
FIG. 4 is a rear view illustrating the placement on a head of the apparatus shown in FIG. 1.
Figure 5:
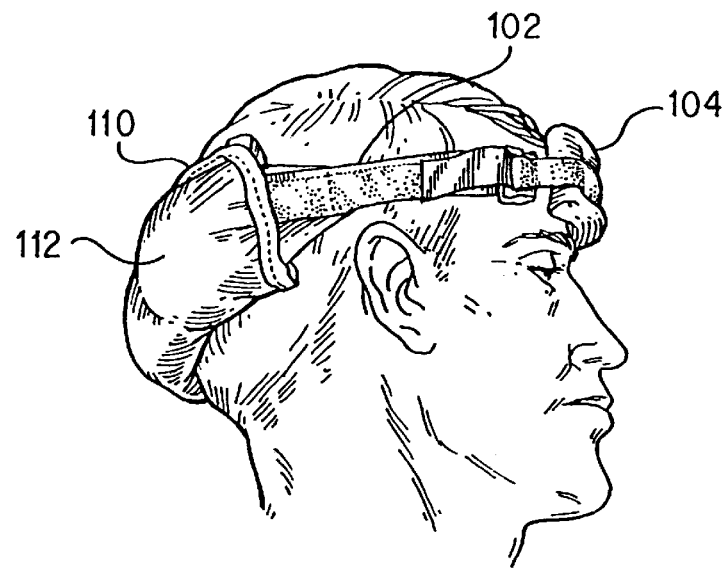
FIG. 5 is a profile view illustrating the placement on a head of the apparatus shown in FIG. 1.

FIGS. 3–5 illustrate how the therapeutic pad relates to the frontal F, parietal P, and occipital O bones. In particular, FIGS. 3 and 4 illustrate how the therapeutic pad contacts the occiput in relation to the primary cranial bones. Although the headband in FIG. 3 is shown making contact with the parietal bones, i.e., the sides of the cranium, the therapeutic pad 110 can be of sufficient width such that, when the band is attached about the ends of the pad, the bands do not contact the head when worn.

The forehead pad 104 can provide cushioning to the forehead to facilitate the comfort when wearing the mounting apparatus. Additionally, the forehead pad 104 can position the therapeutic pad on the cranium such that the force applied to the occiput is at the proper angle and placement. In accordance with the preferred embodiment, the forehead pad 104 should be slightly superior to the frontal eminence. The force of the protrusions 112 that are applied to the occiput can depend on the adjustments to each band 102. The resulting effective force upon the head should be approximately one to five pounds.

In FIG. 4, the two protrusions 112, which are shown with hidden lines, are located at the proper position for applying pressure to the occiput. Preferably, the two protrusions 112 should be equidistant from the midline to the right and to the left on the occiput. The protrusions 112 should be superior to the external occipital nucal ridge, and inferior to the lamboidal suture.

FIG. 5 also illustrates the proper positioning of the headband 100 according to a preferred embodiment. The headband 100 can be worn while standing, sitting, or exercising. With the headband 100 properly in place, a constant pressure can be exerted against the occiput for applying resistance to the dural rhythmic pulsations. The wearer can then experience a relaxing, therapeutic effect while remaining mobile and capable of continuing normal, daily activities.

A variety of other designs and modifications can aid to make the device more fashionable or comfortable while still applying occipital pressure. The therapeutic pad can be positioned with respect to the occiput by means of a hat or a cap, which serves to cover the head and disguise the apparatus from public view.

Figure 6:
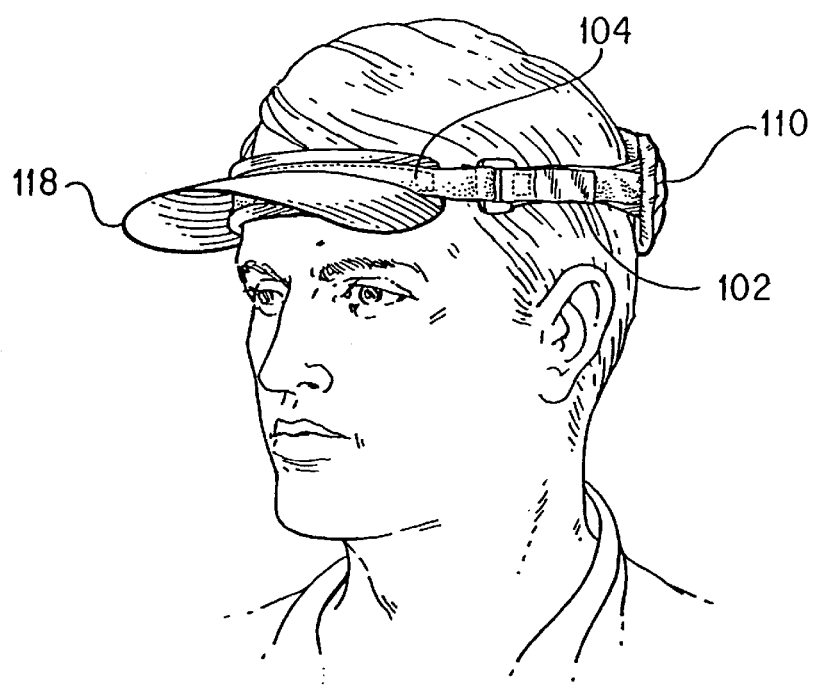
FIG. 6 is a perspective view of another preferred embodiment of an apparatus for applying cranial occipital pressure.

As shown in FIG. 6, the therapeutic pad 110 can be provided in combination with a visor to cover or shade the face while wearing the apparatus. For example, a bill 118 can be attached to the outer surface of the forehead pad 104.

As can be readily understood, the hat or cap would include a harness as part of its structure for holding the therapeutic pad against the occiput. This hat or cap, which can be a modified conventional baseball cap, can include side straps for adjusting the size of the cap for different head sizes or different desired tension levels at the sides of the cap. A conventional hat or cap can also be modified to apply bilateral occipital pressure by inserting therapeutic padding within an inner portion at the back of the cap. The back padding can be temporarily inserted and attachable to the inner portion of the cap by Velcro hook-and-loop fasteners.

When wearing one of the preferred embodiments, the applied bilateral occipital pressure puts the cranium in a state of flexion. In an alternative embodiment, additional pressure points can be applied to the frontal bone in the cranium to enhance the relaxing and therapeutic effects induced by applying occipital pressure. In particular, by supplementing the forehead pad 104 with two projections (not shown), the wearer can also benefit from bilateral frontal compression. Optional removable pads can be added to the inside of a front cushion, or a front portion of a visor or hat to apply bilateral frontal pressure as desired. The frontal pads can be attached (e.g., glued or sewn) onto a removable hook-and-loop Velcro strap that can be affixed to the inner side of the forehead cushion 104. Alternatively, the frontal pads can be directly attached to the inner side of the forehead cushion 104 by Velcro attachments. The frontal pads can be made removable because it may not be desirable in some cases to apply both frontal and occipital pressures.

It is also possible to wear one of the preferred embodiments, e.g., as shown in shown in FIG. 5, in reverse. As such, bilateral pressure would be applied to the frontal bone, and lateral, uniform pressure would be applied to the occiput.

While the present invention has been disclosed with reference to certain preferred embodiments, numerous modifications, alterations, and changes to the described embodiments are possible without departing from the sphere and scope of the present invention, as defined in the appended claims. Accordingly, it is intended that the present invention not be limited to the described embodiments, but that it have the full scope defined by the language of the following claims, and equivalents thereof.

What is claimed is:

1. An apparatus for applying occipital pressure to a human head, the human head having frontal, parietal, and occipital bones, the frontal bone generally being on a front portion of the head, the occipital bone generally being on a back portion of the head, and the parietal bones generally extending between the frontal and occipital bones, the apparatus comprising:

a harness adapted to overlie the frontal bone; and a pad adapted to apply a therapeutic force to the occipital bone, the pad having first and second ends attached to the harness, and having first and second protrusions extending generally toward the harness and adapted to overlie the occipital bone.

2. The apparatus according to claim 1, wherein the harness comprises a cushion adapted to apply a reactive force opposing the therapeutic force.

3. An apparatus for applying occipital pressure to a human head, the human head having frontal, parietal, and occipital bones, the frontal bone generally being on a front portion of the head, the occipital bone generally being on a back portion of the head, and the parietal bones generally extending between the frontal and occipital bones, the apparatus comprising:

a harness adapted to overlie the frontal bone; and a pad adapted to apply a therapeutic force to the occipital bone, the pad having first and second ends attached to the harness, and having first and second protrusions extending generally toward the harness and adapted to overlie the occipital bone;

wherein the harness comprises a cushion adapted to apply a reactive force opposing the therapeutic force, and includes a first band connecting the first end of the pad to the cushion and a second band connecting the second end of the pad to the cushion.

4. The apparatus according to claim 3, wherein at least one band further comprises a strap and a buckle adapted to adjust a band length.

5. The apparatus according to claim 3, wherein at least one band further comprises a hook and loop fastener adapted to adjust a band length.

6. The apparatus according to claim 3, wherein only the pad and the cushion are adapted to apply forces to the head.

7. An apparatus for applying occipital pressure to a human head, the human head having frontal, parietal, and occipital bones, the frontal bone generally being on a front portion of the head, the occipital bone generally being on a back portion of the head, and the parietal bones generally extending between the frontal and occipital bones, the apparatus comprising:

a harness adapted to overlie the frontal bone; and a pad adapted to apply a therapeutic force to the occipital bone, the pad having first and second ends attached to the harness, and having first and second protrusions extending generally toward the harness and adapted to overlie the occipital bone;

wherein the harness comprises a cushion adapted to apply a reactive force opposing the therapeutic force and the cushion further comprises first and second projections adapted to apply bilateral forces to the frontal bones.

8. An apparatus for applying occipital pressure to a human head, the human head having frontal, parietal, and occipital bones, the frontal bone generally being on a front portion of the head, the occipital bone generally being on a back portion of the head, and the parietal bones generally extending between the frontal and occipital bones, the apparatus comprising:

a harness adapted to overlie the frontal bone; and a pad adapted to apply a therapeutic force to the occipital bone, the pad having first and second ends attached to the harness, and having first and second protrusions extending generally toward the harness and adapted to overlie the occipital bone;

wherein the harness comprises a cushion adapted to apply a reactive force opposing the therapeutic force and the cushion further comprises a removable insert to apply bilateral forces, a removable insert comprising first and second projections.

9. The apparatus according to claim 2, wherein the harness further comprises a visor shade extending generally away from the pad.

10. The apparatus according to claim 1, wherein the first and second protrusions of the pad are spaced a distance apart so as to be adapted to apply equal bilateral forces to the occipital bone.

11. An apparatus for applying occipital pressure to a human head, the human head having frontal, parietal, and occipital bones, the frontal bone generally being on a front portion of the head, the occipital bone generally being on a back portion of the head, and the parietal bones generally extending between the frontal and occipital bones, the apparatus comprising:
   a harness adapted to overlie the frontal bone; and
   a pad adapted to apply a therapeutic force to the occipital bone, the pad having first and second ends attached to the harness, and having first and second protrusions extending generally toward the harness and adapted to overlie the occipital bone;
   wherein the harness comprises a cap adapted to overlie at least portions of the frontal, parietal, and occipital bones.

12. An apparatus for applying pressure to a human head, the human head having frontal, parietal, and occipital bones, the frontal bone generally being on a front portion of the head, the occipital bone generally being on a back portion of the head, and the parietal bones generally extending between the frontal and occipital bones, the apparatus comprising:
   a band adapted to surround the human head, the band having a first portion adapted to overlie the occipital bone, a second portion adapted to overlie the frontal bone, and connecting portions extending between the first and second portions;
   a pair of protrusions extending inwardly from the first portion and adapted to apply a therapeutic force to the occipital bone;
   a cushion extending inwardly from the second portion and adapted to apply a reaction force to the frontal bone, the reaction force opposing the therapeutic force; and
   a pad connecting the pair of protrusions.

13. An apparatus for applying pressure to a human head, the human head having frontal, parietal, and occipital bones, the frontal bone generally being on a front portion of the head, the occipital bone generally being on a back portion of the head, and the parietal bones generally extending between the frontal and occipital bones, the apparatus comprising:
   a band adapted to surround the human head, the band having a first portion adapted to overlie the occipital bone, a second portion adapted to overlie the frontal bone, and connecting portions extending between the first and second portions;
   a pair of protrusions extending inwardly from the first portion and adapted to apply a therapeutic force to the occipital bone;
   a cushion extending inwardly from the second portion and adapted to apply a reaction force to the frontal bone, the reaction force opposing the therapeutic force; and
   a pad connecting the pair of the protrusions, wherein the connecting portions comprise first and second bands connecting respecting ends of the pad and the cushion.

14. An apparatus for applying pressure to a human head, the human head having frontal, parietal, and occipital bones, the frontal bone generally being on a front portion of the head, the occipital bone generally being on a back portion of the head, and the parietal bones generally extending between the frontal and occipital bones, the apparatus comprising:
   a band adapted to surround the human head, the band having a first portion adapted to overlie the occipital bone, a second portion adapted to overlie the frontal bone, and connecting portions extending between the first and second portions;
   at least one protrusion extending inwardly from the first portion and adapted to apply a therapeutic force to the occipital bone;
   a cushion extending inwardly from the second portion and adapted to apply a reaction force to the frontal bone, the reaction force opposing the therapeutic force;
   wherein only the at least one protrusion and the cushion are adapted to apply pressure to the head.

* * * * *